United States Patent [19]

White

[11] 4,411,163

[45] Oct. 25, 1983

[54] VENTABLE SAMPLE COLLECTION DEVICE

[75] Inventor: Fred K. White, Miami, Fla.

[73] Assignee: American Hospital Supply Corporation, Evanston, Ill.

[21] Appl. No.: 287,277

[22] Filed: Jul. 27, 1981

[51] Int. Cl.³ .............................................. A61B 5/14
[52] U.S. Cl. ............................. 73/864.02; 128/763; 128/767; 435/296; 215/309; 220/366; 210/927; 604/73; 604/313
[58] Field of Search ............................ 128/763-767, 128/220, 218 S; 73/864.02, 864.72; 435/291, 292, 296; 215/309, 307; 220/366; 210/DIG. 24, 927

[56] References Cited

U.S. PATENT DOCUMENTS

| | | | |
|---|---|---|---|
| 234,342 | 11/1880 | Stewart | 215/307 |
| 261,465 | 7/1882 | Levy | 220/366 X |
| 1,581,072 | 4/1926 | Tumsden | 215/309 X |
| 2,423,295 | 7/1947 | Crabbe et al. | 220/366 X |
| 2,629,421 | 2/1953 | Ayres | 220/366 X |
| 2,655,152 | 10/1953 | Turner | 128/276 |
| 3,010,596 | 11/1961 | Williams et al. | 215/307 X |
| 3,021,029 | 2/1962 | McKinlay | 220/366 X |
| 3,181,529 | 5/1965 | Wilburn | 128/764 |
| 3,222,114 | 12/1965 | Portnsy | 128/765 |
| 3,248,025 | 4/1966 | Santore | 215/309 X |
| 3,297,184 | 1/1967 | Andelin | 435/296 |
| 3,513,829 | 5/1970 | Deuschee | 128/767 |
| 3,718,133 | 2/1973 | Perry | 128/765 |
| 3,776,218 | 12/1973 | Svensson | 210/DIG. 24 X |
| 3,902,477 | 9/1975 | Gerarde | 128/760 |
| 3,963,120 | 6/1976 | Perfect | 220/366 X |
| 4,024,857 | 5/1977 | Beecher | 128/763 |
| 4,036,387 | 7/1977 | Feaster | 215/309 |
| 4,250,893 | 2/1981 | White | 128/765 |
| 4,278,437 | 7/1981 | Haggar | 128/764 X |

*Primary Examiner*—Kyle L. Howell
*Assistant Examiner*—Nancy A. B. Swisher
*Attorney, Agent, or Firm*—Tilton, Fallon, Lungmus

[57] ABSTRACT

A device for collecting samples of blood and other fluids for clinical testing purposes. The device includes an open-ended vial and a cap equipped with a capillary tube for drawing samples into the wall. The cap is internally threaded and the vial is provided at its open end with at least one arcuate flange engagable with the threads of the cap to shift the parts axially as they are rotated with respect to each other. A vent opening in the cap is sealed by the flange when the parts are threaded tightly together and is unsealed to allow passage of air to and from the vial when the parts are unthreaded but still connected. Retention lips provided by the cap retain the parts together when they are in their unthreaded condition.

17 Claims, 6 Drawing Figures

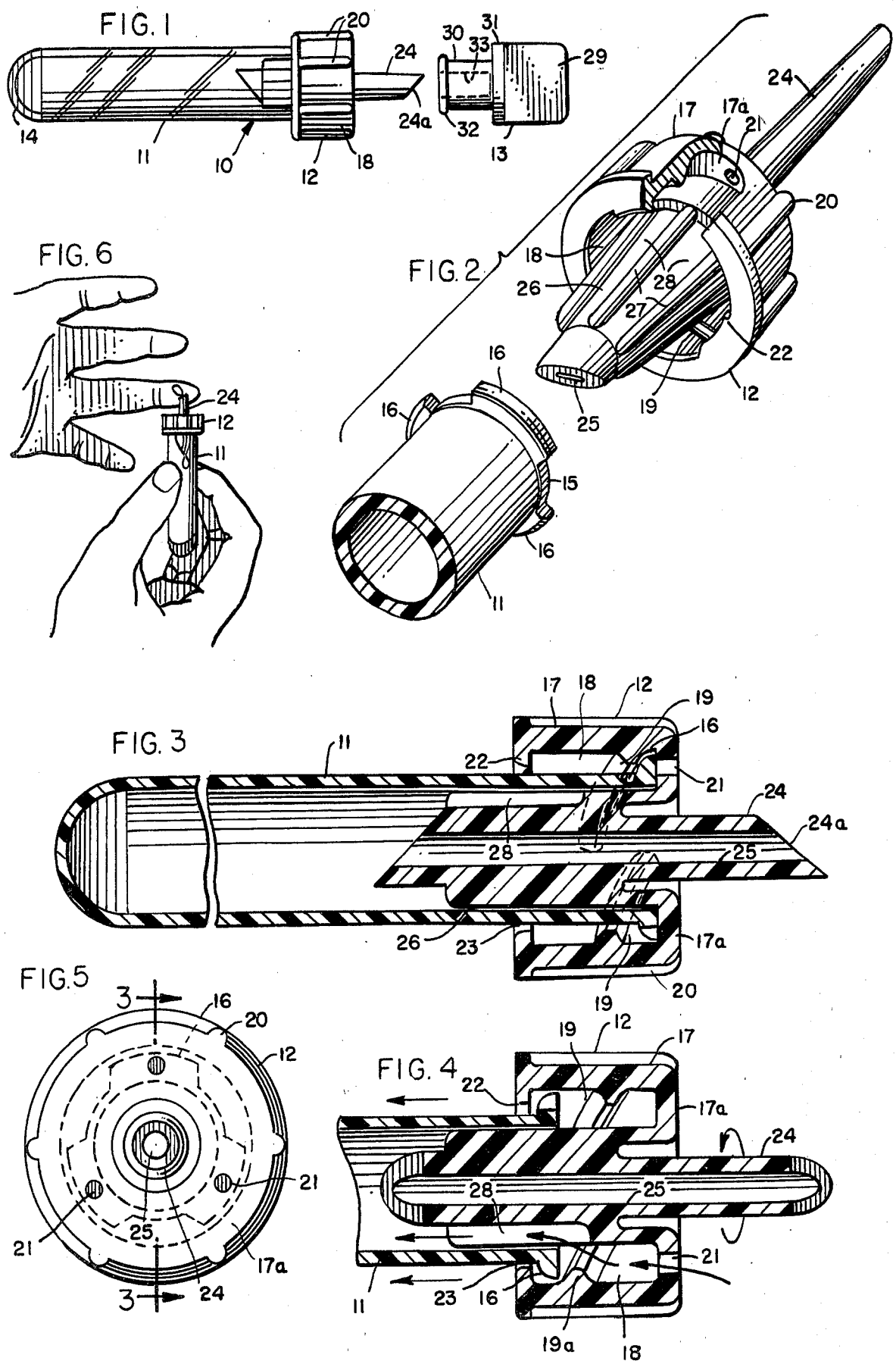

VENTABLE SAMPLE COLLECTION DEVICE

BACKGROUND OF THE INVENTION

Co-owned U.S. Pat. No. 4,250,893 discloses a sample collecting device having a deformable vial and a non-vented cap removably secured to the open end of the vial. A bevel-tipped collection tube extends from the end wall of the cap and is used to draw blood or other sample fluids into the vial when the deformable plastic vial is squeezed between the fingers and then released. As the flexible plastic vial recovers its original configuration, a suction effect is produced to draw the fluid through the collection tube and into the vial.

For such an operation, the device must be non-vented, since otherwise the suction effect would not be generated to draw fluid into the vial through the collection tube. Consequently, the non-vented construction of the device effectively precludes its use in drawing samples by capillary action in contrast to aspiration.

Fluid collection devices that are vented and are filled by gravity and/or capillary action are known but, because they are vented, such devices may present problems in connection with the sealing of such a sample after it has been collected. For example, U.S. Pat. No. 4,024,857 discloses a device that consists essentially of a rigid vial, a vented cap which has a capillary tube for drawing the blood sample into the vial, and in the commercial form of the device, a plug to replace the cap for purposes of sealing the vial after a blood sample has been taken. Following the drawing of a sample, a user must replace the cap with the plug in order to mix the sample with anticoagulant already present in the vial and to prevent contamination or loss of the contents of the vial during subsequent storage and handling. Such manipulative steps are cumbersome, time-consuming, and clearly undesirable not only because they increase the risks of contamination of the blood sample but also because they increase the chances that the user might accidentally touch the blood sample and become contaminated by pathogens in that sample.

Other patents reflecting the state of the art are U.S. Pat. Nos. 3,902,477, 3,181,529, 3,513,829, 3,718,133, 3,322,114, and 2,655,152.

SUMMARY OF THE INVENTION

One aspect of this invention lies in providing a sample collecting device which is vented for filling by gravity/capillary flow but which may be easily and quickly adjusted into a non-vented condition for storage or transit of a collected specimen or, if the device is so adapted, for collection of a fluid specimen by squeezing and releasing the vial to create a suction in the manner described in U.S. Pat. No. 4,250,893. Another object is to provide a vial and cap which, by relative rotation of the parts, may be readily adjusted to seal and unseal one or more vents so that the device may be either vented or unvented depending on the requirements of use.

Briefly, the device takes the form of a generally cylindrical plastic vial provided with an opening at one end, and a cap adapted to fit over the open end. The cap is equipped with a sample collection tube for drawing a sample of blood or other fluid into the vial. The interior of the cap is threaded, and the vial is provided with at least one laterally-projecting arcuate flange or tongue adapted to engage the threads for urging the cap and vial axially when the parts are rotated with respect to each other. The flange or tongue performs the further function of sealing a vent opening in the end wall of the cap when the parts are threaded tightly together or, conversely, unsealing that opening when the parts are rotated into a partially separated condition. Retention lips are provided by the cap to engage the flange(s) of the vial and resist complete separation of the parts. Such resistance may be overcome by forces sufficiently strong to cause limited flexure or distortion of the lips.

A closure element is provided to receive and seal the collection tube of the cap in the manner described in U.S. Pat. No. 4,250,893. When the closure element is in place on the collection tube and the cap and vial have been rotated to seal the vent, the contents of the sample collection device are fully sealed against exposure and contamination. Should removal of the cap from the tubular vial be desired, the closure element may be reversed and inserted into the opening of the vial to provide a secure closure in the manner described in the aforementioned U.S. Pat. No. 4,250,893.

An important advantage over the construction of the aforementioned patent lies in the fact that this device may be filled by capillary/gravity action. If that is the only mode of filling contemplated, then the vial may be formed of relatively rigid plastic material. On the other hand, if filling by suction is also desired, then the vial may be formed of deformable plastic and, by rotating the cap one way or the other to open or close the vent(s), the device may be filled either by capillary/gravity flow or by suction.

Other features, advantages, and objects of the invention will become apparent from the specification and drawings.

DRAWINGS

FIG. 1 is a side elevational view of a fluid collection device embodying the present invention.

FIG. 2 is a fragmentary enlarged exploded perspective view of the vent-providing cap and the portion of the vial cooperable therewith.

FIG. 3 is an enlarged longitudinal sectional view showing the cap and vial with the vents in sealed condition.

FIG. 4 is a view similar to FIG. 3 but showing the parts adjusted so that the vents are unsealed.

FIG. 5 is an end elevational view of the cap showing (in broken lines) the vial adjusted to seal the cap's vent openings.

FIG. 6 is a view illustrating use of the device in the collection of a blood sample.

DETAILED DESCRIPTION

Referring to the drawings, the numeral 10 generally designates a blood collection device comprising a tubular vial 11, a cap 12 attached to the vial, and a closure element 13 (FIG. 1) adapted to cooperate with either the cap or the vial to perform a sealing function. The vial takes the form of an elongated tubular body having a closed end 14 and an open end 15. The open end portion is provided with at least one outwardly-projecting arcuate flange or tongue 16. A plurality of such flanges are shown in the drawings (FIGS. 2, 5); while three such flanges are depicted, it will be understood that a greater or lesser number of such circumferentially-spaced flanges may be provided.

The vial may be formed of relatively rigid (but non-brittle) polymeric material, or from readily deformable but shape-recoverable plastic, depending on the method (or methods) of filling desired to be used. If gravity/capillary fill is the only filling technique contemplated, then a more rigid material may be used, whereas if it is also desired to have the device fillable by a suction technique as disclosed in co-owned U.S. Pat. No. 4,250,893, then a more flexible plastic material should be selected. For example, high density polypropylene is believed suitable for a relatively rigid vial to be filled by capillary action; lower density polypropylene or polyethylene may be used where flexibility is to be provided for a suction-filling capability. Whatever the selection, the material should have sufficient clarity so that the wall of the vial is generally transparent. As used herein, the terms "transparent" is intended to include any material having sufficient clarity to permit the contents of the vial to be viewed through the wall of that vial; hence, milky, tinted, or even translucent materials may be suitable for that purpose.

The cap 12 includes a cup-shaped body portion 17 defining a cavity 18 for receiving the end portion 15 of the vial. Internal threads 19 are engagable with lugs 16 to permit the cap to be screwed tightly over the open end portion of the vial. Internal threads 19, three in number, are engagable with the three flanges 16 to permit the cap to be screwed tightly upon the open end of the vial. External longitudinal ribs 20 may be provided as shown to assist a user in gripping the cap for tightening as well as for attachment and detachment.

The end wall 17a of the cap is provided with at least one vent opening 21. Three such openings are depicted in the drawings, although a greater or smaller number may be provided as desired. In any event, the number of vent openings 21 should match the number of flanges or tongues 16 of vial 11, and such openings should be positioned and arranged so that when the cap and vial are screwed tightly together the flanges 16 will be aligned with and seal each of the vent openings 21 (FIGS. 3, 5). Hence, the flanges or tongues 16 perform the dual functions of cooperating with threads 19 to guide the vial axially within the cap as the parts are rotated with respect to each other and, when they are fully tightened, to seal vent openings 21.

The flanges also perform a third function as indicated in FIG. 4. Retention lips 22 border the mouth 23 of the cap and the opening defined by such lips is slightly smaller than the flanged end of the vial. Since the circumferential distance between adjacent lips 22 is less than the corresponding distance between adjacent flanges 16, the vial cannot be withdrawn from the cap without flexure or distortion of lips 22, or flanges 16, or both. The interference is sufficient only to exert a limited retentive force to prevent inadvertent detachment of the cap from the vial. To enhance flexibility, a plurality of circumferentially-spaced lips are provided rather than a single continuous lip; however, the latter might be acceptable if the material of the cap is sufficiently yieldable to permit lip distortion when the parts are to be separated or assembled.

Cap 12 may be formed of any suitable flexible plastic material. A polyolefin, particularly polypropylene, has been found effective, but other polymeric materials having similar properties may be used.

The cap has an elongated collection or capillary tube portion 24 projecting outwardly and axially from the end wall 17a. Preferably the outer tube portion 24 has a beveled tip 24a as shown most clearly in FIGS. 1 and 3. The lumen 25 of the collection tube extends through the end wall of the cap and, in the embodiment depicted in the drawings, a tubular inner extension 26 projects into and beyond the cavity 18 of the cap to direct the flow of fluid into vial 11. Like the outer collection tube portion 24, the inner tube portion or extension 26 is coaxial with the remainder of the cap and may be beveled at its free end. Ideally, the inner and outer tubular portions are formed integrally with other portions of the cap, although the parts might be formed separately and later fused or otherwise sealed together. In any event, the final result is a unitary cap which is internally threaded and vented. The inner tubular portion 26 is provided with a plurality of longitudinal external ribs 27 which define longitudinal channels 28 therebetween; such channels are of sufficient length to place the interior of the vial in communication with cavity 18 when the vial is in its retracted or unthreaded condition illustrated in FIG. 4. Although threads 19 may extend the full length of cavity 18, it has been found beneficial to terminate each thread at a point spaced axially from retention lips 22, thereby providing a limited free zone between the lips and threads in which the flanges 16 of the vial are disengaged from the threads but are nevertheless retained within the cap. Thus, referring to FIG. 4, the numeral 19a represents the end of the lower thread, and the flanges 16 of vial 11 are therefore shown within the zone between the ends of the threads and retention means 22.

Closure member 13 includes a handle portion 29, a sleeve portion 30, and a shield portion 31. The sleeve portion is generally cylindrical and has an external annular rib 32 dimensioned to make fluid-tight sealing contact with the inner surface of vial 11 at the mouth end thereof. The sleeve also has an axial recess 33 for snugly and sealingly receiving the tip portion 24a of the tapered collection tube portion 24. Thus, when the tip of the collection tube portion is inserted into the blind recess 33, and the vial is screwed into the cap until its radial flanges 16 engage the cap's end wall 17a and seal vent openings 21, the content of the vial will be sealed against escape and against external contaminants.

Handle portion 29 takes the form of a wing-like tab disposed in a longitudinal and diametrical plane. In structure and operation, closure 13 is similar to the closure of co-owned U.S. Pat. No. 4,250,893, and reference may be had to that patent for further discussion of the structure, use, and advantages of such a closure.

FIG. 6 illustrates the collection device in use in the drawing of a microsample of blood. If the cap and vial were previously rotated into their unthreaded positions to expose vent openings 21, then the blood sample passes through the collection tube and into the vial under the influence of capillary forces, gravity, or both. No squeezing or deformation of vial 11 is required in the drawing of such a sample; if the device is intended to be filled only by capillary/gravitational forces, then as already described the vial may be formed of relatively rigid material. Following the taking of the sample, the operator simply slips closure member 13 over the tapered tip 24a, screws the vial and cap into the positions shown in FIG. 3, and thereby seals the collected blood sample within the vial. Alternatively, the user may completely remove cap 12 from the vial 11 and replace the cap with closure member 13.

If suction filling of the device is desired, in contrast to capillary/gravity filling, and if the vial 11 is formed of deformable material capable of returning to its original configuration when squeezing forces are relieved, then the user may simply screw the vial and cap together (FIG. 3) prior to the sample-drawing procedure, expel air from the vial by squeezing its walls together, and then draw a blood sample into the vial while at the same time allowing the wall of the vial to return to its original undeformed condition (FIG. 6).

While in the foregoing I have disclosed an embodiment of the invention in considerable detail for purposes of illustration, it will be understood by those skilled in the art that many of these details may be varied without departing from the spirit and scope of the invention.

I claim:

1. A device for collecting fluid samples for laboratory use, comprising an open-ended vial having at least one arcuate flange projecting outwardly therefrom at said open end; a cap having a generally cylindrical side wall and an end wall defining a cavity removably received on the open end of said vial; said cap having an elongated collection tube portion projecting outwardly from said end wall and an inner tube portion disposed within said cavity and aligned with said collection tube portion; said cap also having at least one internal thread provided by the inner surface of said side wall and engagable by said flange for directing said vial axially when said flanged end of the vial is rotated within said cavity; said end wall having a vent opening therethrough; said vent opening being positioned and arranged to be sealed by said flange when said open end of said vial is fully threaded into said cavity of said cap.

2. The device of claim 1 in which said vial is provided with a plurality of said flanges spaced circumferentially apart at said open end, and said cap is provided with a plurality of said vent openings positioned and arranged to be sealed by said flanges when said vial is fully threaded into said cavity.

3. The device of claim 1 in which said vial is cylindrical in shape.

4. The device of claim 3 in which said inner tube portion of said cap extends axially beyond said cavity.

5. The device of claim 4 in which said inner tube portion has longitudinally-extending external ribs defining channels therebetween for the passage of air from said vial through said vent opening when said opening is unsealed.

6. The device of claim 1 in which said inner and outer tube portions are formed integrally with the remainder of said cap.

7. The device of claim 6 in which said cap is formed of flexible plastic material.

8. The device of claim 1 in which said cap is provided with at least one retention lip at the opening to said cavity, said lip being flexible and being engagable with said flange to retain said vial and cap together unless forces are applied sufficient to deform said lip and allow removal of said vial from said cap.

9. The device of claims 1, 3, 4, or 5 in which said vial is formed of substantially rigid plastic material.

10. The device of claims 1, 3, 4, or 5 in which said vial is formed of flexible material and is capable of being deformed by finger pressure applied thereto, and recovering its original shape when such pressure is relieved, to draw fluid therein when said vent is sealed.

11. A device for collecting fluid samples for laboratory use, comprising a generally cylindrical vial formed of substantially rigid plastic material and having an opening at one end thereof; said vial also having a plurality of circumferentially-spaced flanges projecting outwardly therefrom at said one end; a cap removably received on said vial having a generally cylindrical side wall and an end wall defining a cavity for receiving said one end of said vial; said cap having an elongated collection tube portion projecting outwardly from said end wall and an inner tube portion disposed within said cavity and aligned with said collection tube portion; said cap also being internally threaded with the threads thereof engagable by said flanges for directing said vial axially when said one end thereof is rotated within said cavity; said end wall having at least one vent opening therethrough; said vent opening being positioned and arranged to be sealed by a flange of said vial when said one end of said vial is fully threaded into said cavity of said cap.

12. The device of claim 11 in which said cap is provided with a plurality of said vent openings positioned and arranged to be sealed by said plurality of flanges when said vial is fully threaded into said cavity.

13. The device of claim 11 in which said inner tube portion of said cap extends axially beyond said cavity.

14. The device of claim 13 in which said inner tube portion has longitudinally-extending external ribs defining channels therebetween for the passage of air from said vial through said vent opening when said opening is unsealed.

15. The device of claim 11 in which said inner and outer tube portions are formed integrally with said cap.

16. The device of claim 11 in which said cap is provided with at least one retention lip at the opening to said cavity; said lip being flexible and being engagable by said flanges to retain said vial and cap together unless forces are applied sufficient to deform said lip and allow removal of said vial from said cap.

17. The device of claim 16 in which there are a plurality of said retention lips.

* * * * *